United States Patent [19]

Chinn

[11] Patent Number: 4,694,018
[45] Date of Patent: Sep. 15, 1987

[54] SUBSTITUTED 1,5-DIPHENYL-2-PYRROLEPROPIONIC ACIDS AND DERIVATIVES

[75] Inventor: Leland J. Chinn, Glenview, Ill.

[73] Assignee: G. D. Serale & Co., Chicago, Ill.

[21] Appl. No.: 802,885

[22] Filed: Nov. 29, 1985

[51] Int. Cl.$^4$ .................. C07D 207/337; A61K 31/40
[52] U.S. Cl. .................... 514/427; 514/825; 514/826; 514/886; 548/561; 548/562
[58] Field of Search ............... 548/561, 562; 514/427, 514/886, 825, 826

[56] References Cited

U.S. PATENT DOCUMENTS

| | | | |
|---|---|---|---|
| 3,168,527 | 2/1965 | Short | 548/562 |
| 3,168,529 | 2/1965 | Short | 260/326.3 |
| 3,168,531 | 2/1965 | Short | 548/562 |
| 3,168,532 | 2/1965 | Short | 548/562 |
| 3,471,513 | 10/1969 | Chinn | 260/326.3 |
| 3,475,451 | 10/1969 | Chinn | 260/326.3 |
| 3,542,788 | 11/1970 | Chinn et al. | 260/294 |

FOREIGN PATENT DOCUMENTS 998996  7/1965  United Kingdom ............... 548/562

*Primary Examiner*—Mark L. Berch

*Attorney, Agent, or Firm*—Mary Jo Kanady; Paul D. Matukaitis

[57] ABSTRACT

The compounds of the present invention comprise substituted 1,5-diphenyl-2-pyrrolepropionic acids and derivatives thereof represented by the formula:

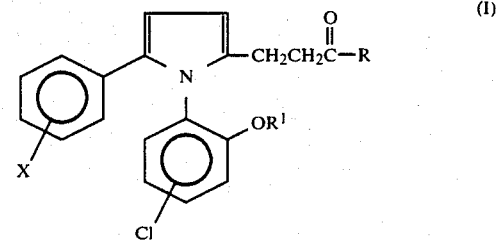

wherein: R represents hydroxy, alkoxy of from 1 to 6 carbon atoms, inclusive, or amino; $R^1$ represents hydrogen or acyl of from 2 to 7 carbon atoms, inclusive; and X represents hydrogen, halogen, hydroxy or alkoxy of from 1 to 6 carbon atoms, inclusive. The compounds of the present invention are 5-lipoxygenase inhibitors and, therefore, are useful in the treatment of local and systemic inflammation, allergy and hypersensitivity reactions and other disorders in which agents formed in the 5-lipoxygenase metabolic pathway are involved.

12 Claims, No Drawings

SUBSTITUTED 1,5-DIPHENYL-2-PYRROLEPROPIONIC ACIDS AND DERIVATIVES

BACKGROUND OF THE INVENTION

A. Field of the Invention

The present invention relates to substituted 1,5-diphenyl-2-pyrrolepropionic acids and derivatives and more particularly relates to the novel compounds of formula I which are specific 5-lipoxygenase inhibitors and are useful as anti-inflammatory and anti-allergy agents.

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects. The leukotrienes, which are produced via the 5-lipoxygenase pathway, are the major contributors to the onset of the symptoms of asthma, and mediators for immediate hypersensitivity reactions and inflammation.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other immediate hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only cheomtactic for neutrophils and monocytes, but is also highly active in stimulating eosinophil locomotion. $LTB_4$ also stimulates calcium influx and aggregation of polymorphonuclear leukocytes and $LTB_4$ may, thus, play an important role in mediating both acute and chronic inflammation.

Rheumatiod spondylitis is characterized by an acute neutrophil flare in the joint which is associated with elevated levels of $LTB_4$. $LTB_4$ is also present in gouty effusions; and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases.

Aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, antipyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced inflammatory effects. Administration of the NSAIDs alone can produce allergic reactions including bronchospastic reactivity; skin rashes; syndrome of abdominal pain, fever, chills, nausea and vomiting; and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs. Co-administration of the 5-lipoxygenase inhibitors of this invention with cyclooxygenase inhibitors may mitigate the untoward side effects of the latter and allow the increased advantageous use of such cyclooxygenase inhibitors.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides substituted 1,5-diphenyl-2-pyrrolepropionic acid and derivatives which are inhibitors of the 5-lipoxygenase pathway and are useful in the treatment of asthma, rheumatoid arthritis, psoriasis, and other allergy, hypersensitivity reactions, and inflammatory conditions.

See Bengt Sameusson, "Leukotrienes: Mediators of Immediate Hypersensitivity Reactions and Inflammation", *Science,* Vol. 220, pp. 568–575 (May 1983); Michael K. Bach, "Inhibitors of Leukotriene Synthesis and Action", *The Leukotrienes, Chemistry and Biology,* pp 163–194 (Academic Press, Inc., 1984); C. W. Lee et al., "Human Biology and Immunoreactivity of Leukotrienes", *Advances in Inflammation Research,* Volume 6, pp 219–225 (Raven Press, New York 1984); Editorial, "Leukotrienes and other Lipoxygenase Products in the Pathogenesis and Therapy of Psoriasis and Dermatoses", *Arch. Dermatol,* Vol. 119, pp 541–547 (July, 1983); Robert A. Lewis et al., "A Review of Recent Contributions on Biologically active Products of Arachidonate Conversion", *Int. J. Immunopharmac.,* Vol. 4, No. 2, pp 85–90 (1982); Michael K. Bach, *Biochemical Pharmacology,* Vol. 23, No. 4, pp 515–521 (1984); and E. L. Becker, *Chemotactic Factors of Inflammation,* pp 223–225 (Elsevier Science Publishers V.B., Amsterdam, 1983); Sharon, P. and Stenson, W. F., *Gastroenterology,* Vol. 84, 454 (1984); and Musch, M. W. et al., *Science,* Vol. 217, 1255 (1982).

The present invention provides compounds which block the 5-lipoxygenase metabolic pathway and, therefore, block the formation of the leukotrienes resonsible for allergy and inflammation, and represent a new class of therapeutic agents which are useful in the treatment of allergic and hypersensitivity reactions and inflammation, alone, or also may be utilized in combination with cyclooxygenase inhibitors such as the non-steroidal anti-inflammatory agents.

B. Prior Art

Chinn, U.S. Pat. No. 3471513, discloses 2-(2-carboxyethyl)-5-phenyl-1-pyrrole-butyric acid and congeners and the antibiotic and ulcer-inhibiting properties of same.

Chinn, U.S. Pat. No. 3475451 discloses 5-substituted phenyl-2-pyrrolepropionamides and derivatives of the formula

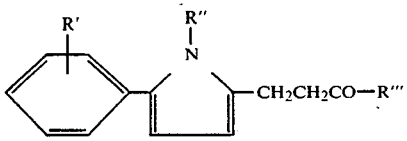

as having analgesic, anti-bacterial and anti-algal properties.

U.S. Pat. No. 3542788, Chinn et al., discloses compounds of the formula

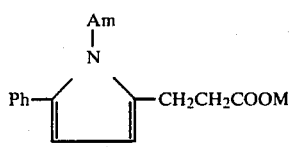

in which AM represents an amino radical, M represents hydrogen or alkyl, and Ph represents phenyl optionally substituted by halogen and/or alkoxy. The foregoing compounds are disclosed as having anti-protozoal, anti-bacterial, anti-inflammatory, and anti-ulcerogenic properties.

U.S. Pat. No. 3168529 discloses anti-inflammatory 1-(p-lower alkanoylphenyl)-5-arylpyrrole-2-propionic acids of the formula:

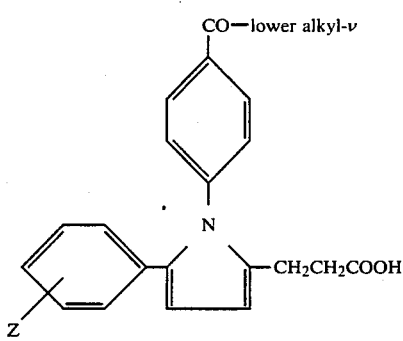

in which Z represents hydrogen, halogen, lower-alkyl, alkoxy or alkylthiol.

In contrast to the above described prior art compounds, the compounds of the present invention contain a substituted phenol directly attached to the pyrrole nitrogen in which the hydroxy group thereof (or precursor) is ortho to the nitrogen atom, i.e.

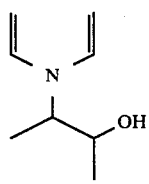

which configuration has now been found to be essential to obtaining the desired 5-lipoxygenase inhibitory activity in these pyrrole derivatives. Moreover, the resultant 5-lipoxygenase inhibitory properties of the present compounds and their ultimate utility in the treatment of inflammation and allergic or hypersensitivity conditions, e.g. asthma, are not disclosed in the foregoing prior art.

SUMMARY OF THE INVENTION

It is, therefore, a primary object of the present invention to provide novel substituted 1,5-diphenyl-2-pyrrolepropionic acids and derivaties thereof.

It is a further object of the present invention to provide methods for promoting anti-allergic and anti-inflammatory effects in mammals in need thereof by the administration of preselected dosages of the compounds of the present invention or pharmaceutically acceptable salts thereof in appropriate non-toxic pharmaceutical dosage forms or compositions.

Another object of the present invention is to provide dosage unit forms adapted for, e.g., oral and/or parenteral administration and useful in the treatment, management and mitigation of allergies, inflammation and hypersensitivity reactions and related disorders and conditions in which physiologically active agents formed in the 5-lipoxygenase metabolic pathway are involved.

DETAILED DESCRIPTION OF THE PREFERRED EMBODIMENTS

These and other similar objects, advantages and features are accomplished according to the products, compositions and methods of the invention comprised of compounds of the formula

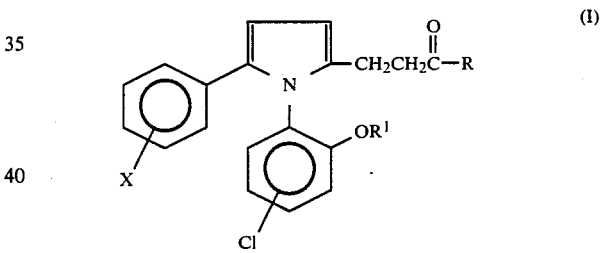

and the pharmaceutically acceptable salts thereof wherein R repesents hydroxy, alkoxy of from 1 to 6 carbon atoms, inclusive, or amino; $R^1$ represents hydrogen or acyl of from 2 to 7 carbon atoms, inclusive; and X represents hydrogen, halogen, hydroxy, or alkoxy of from 1 to 6 carbon atoms, inclusive.

The term "alkoxy" refers to alkoxy groups having 1 to 6 straight or branched chain carbon atoms, i.e., methoxy, ethoxy, n-propoxy, t-butyloxy, etc.

The term "halogen" as used herein, includes chloro, bromo, iodo and fluoro with chloro and fluoro being preferred.

The term "acyl" refers to the residue of the corresponding organic acids absent the hydroxyl group thereof having from 2 to 7 carbon atoms including the carbonyl carbon and refer to, for example, acetyl, propionyl, butyryl, valeroyl, hexanoyl, etc. The compounds of formula I wherein $R^1$ is acyl as defined represent pro-drug forms of the active phenolic derivatives. The term "pro-drug" as used herein denotes compounds which by enzymatic and/or chemical metabolic cleavage releases the active parent drug form in the treated mammal and the cleaved moiety remains non-toxic and metabolized in such a manner that non-toxic metabolic products are produced. These novel pro-drug forms are often advantageous in alterning bioavailability or solubility properties when desired to augment delivery of the final active compounds of the invention.

The expression "pharmaceutically acceptable salts" is intended to include those salts capable of being formed with the compounds of the present invention, e.g., when R represents hydroxy, without materially altering the chemical structure or pharmacological properties thereof. Such salts include inorganic and organic cations, such as sodium, potassium, calcium, ammonium, alkylammonium, etc. well known to those skilled in the art.

The compounds of the present invention can be administered in such oral dosage forms as tablets, capsules, pills, powders, granules, elixirs, or syrups as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the condition. Dosages of the compounds of the present invention, will range generally between about 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered topically to treat proliferative skin conditions such as psoriasis. The daily dosage may be administered in a single dose or in equal divided doses three or four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable insert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of the invention are easily prepared from readily available starting materials in a conventional manner. In general, an appropriately substituted dioxoheptanoic acid is reacted with 2-amino chlorophenol in the presence of p-toluene-sulfonic acid monohydrate to obtain the N-phenolic substituted pyrrole derivatives of the present invention followed by appropriate derivatization reactions, as necessary, to obtain the compounds of Formula I. The foregoing reaction may be schematically represented as follows:

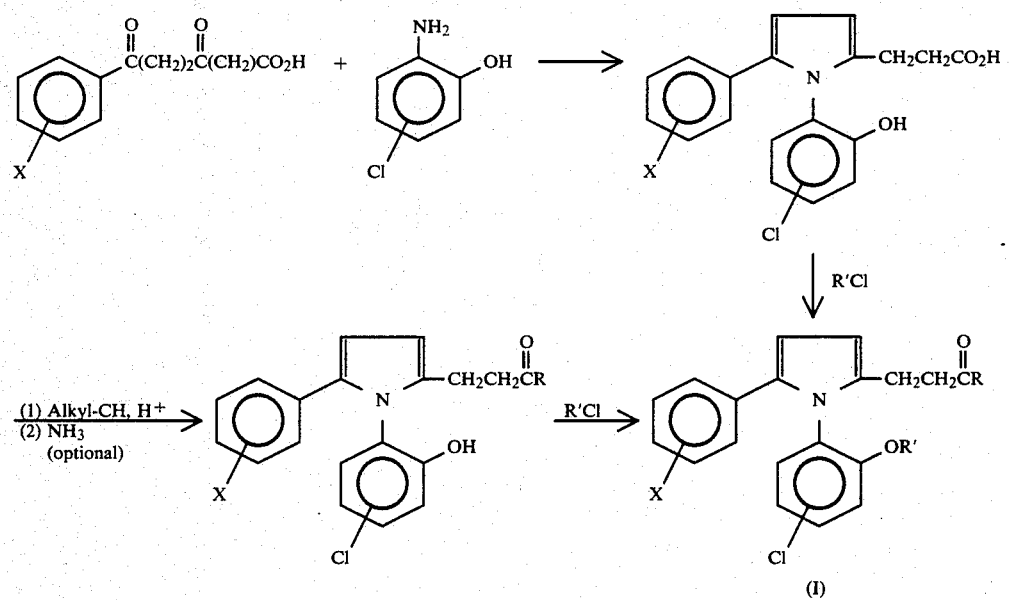

It will be appreciated by those skilled in the art that the substituent X and the chloro group on the phenolic ring may be ortho, meta or para to the point of ring attachment to the pyrrole moiety. To obtain these position isomers, it will be course be necessary to approriately select starting reactants. In accordance with the practices of the present invention, however, the specific ring position of these substituents is not critical to accomplishing the purposes of the invention although X in the para position ahd chloro in the meta position are presently preferred.

The following non-limiting examples further illustrate details for the preparation of the compounds of the present invention. Those skilled in the art will readily understand and appreciate that known variations of the conditions and procedures in the following preparative methods can be utilized. All temperatures are degrees Celcius unless otherwise noted. Melting points were determined on a Thomas-Hoover melting point apparatus and are uncorrected. Chenical shifts are reported in parts per million ($\gamma$) downfield. Splitting patterns are designated as s, singlet; d, doublet; t, triplet; q quartet; and m, multiplet.

EXAMPLE 1

1-(5-chloro-2-hydroxyphenyl)-5-(4-fluorophenyl)-1H-pyrrole-2-propanoic acid

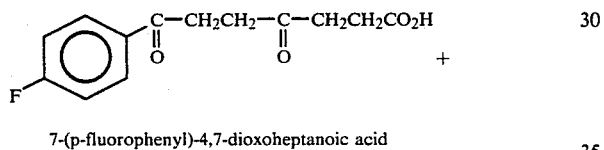

7-(p-fluorophenyl)-4,7-dioxoheptanoic acid
1

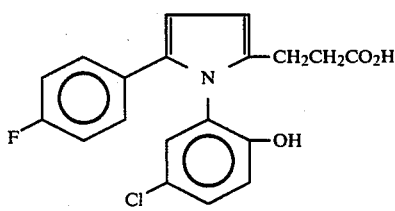

2

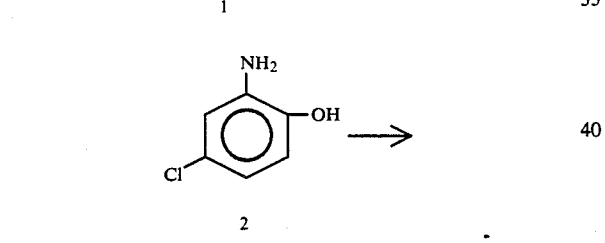

A mixture of 9.6 g of the diketoacid (1), 6.5 g of 2-amino-4-chlorophenol (2), 500 ml of toluene, and 85 mg of p-toluenesulfonic acid monohydrate was stirred and heated under reflux in the presence of a water separator for 19 hours. The reaction mixture was concentrated under reduced pressure to remove almost all of the toluene. The residual oil was crystallized from ether to afford the title product, mp 164°-166°.

Calcd. for $C_{19}H_{15}FClNO_3$ (MW 359.78): C, 63.42; H, 4.20; N, 3.89; Cl. 9.86. Found: C, 63.41; H, 4.21; N, 3.90; Cl. 9.69.

EXAMPLE 2

1-[2-(acetyloxy)-5-chlorophenyl]-5-(4-fluorophenyl)-1H-pyrrole-2-propanoic acid

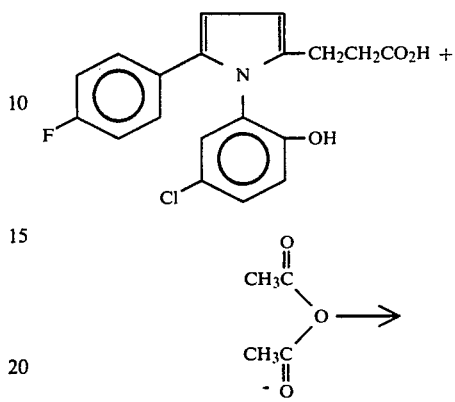

3

A solution of 1.33 g of the compound of Example 1, 15 ml of pyridine, and 18 ml of acetic anhydride was allowed to stand at room temperature for 24 hours. The reaction mixture was poured into 2 L. of ice water. The oil that separated out was rubbed whereupon it solidified. The solid was collected, washed with H$_2$O, and dried. It was crystallized from ether-hexane to afford the anhydride 3, mp 95°-97°.

Calcd. for $C_{23}H_{19L\ NFClO_5}$ (MW 443.95): C, 62.23; H, 4.31; N, 3.16. Found: C, 62.39; H, 4.52; N, 3.17. IR (CHCl$_3$): 1815, 1760, 1593, 1558 cM$^{-1}$.

NMR (CDCl$_3$):

$\delta$1.95 (S, Ar—O$\overset{O}{\overset{\|}{C}}$CH$_3$), 2.19 (S, —$\overset{O}{\overset{\|}{C}}$O$\overset{O}{\overset{\|}{C}}$CH$_3$), 2.73 (S, CH$_2$CH$_2$), 6.05 (d.J-4 Hz, pyrrole-H), 6.25 (d,J-4 Hz pyrrole-H).

The mother liquor resulting from the crystallization of (3) was evaporated to dryness. The residual oil was chromotgraphed on 20 g of silica gel. The column was eluted with dichloromethane to afford a viscous oil. The oil was covered with water. After 0.5 hour the aqueous solution was decanted. The wet residual oil was allowed to stand at room temperature until it began to crystallize. During this process the anhydride (3) underwent partial hydrolysis to furnish the title product. Trituration of the partially crystalline mixture with ether-hexane gaven the desired product, mp 112°–119°.

Calcd. for $C_{21}H_{17}NClFO_4$ (MW 401.82): C, 62.95; H, 4.32; N, 3.39. Found: C, 62.77; H, 4.27; N, 3.49 IR (KRr): 1773, 1715, 1600 cM$^{-1}$.

NMR (CDCl$_3$):

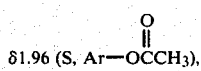

$\delta$1.96 (S, Ar—OCCH$_3$), 2.65 (S, CH$_2$CH$_2$), 6.05 (d,J-4 Hz pyrrole-H), 6.26 (d,J-4 Hz, pyrrole-H).

EXAMPLE 3

1-(5-chloro-2-hydroxyphenyl)-5-(4-fluorophenyl)-1H-pyrrole-2-propanoic acid, methyl ester

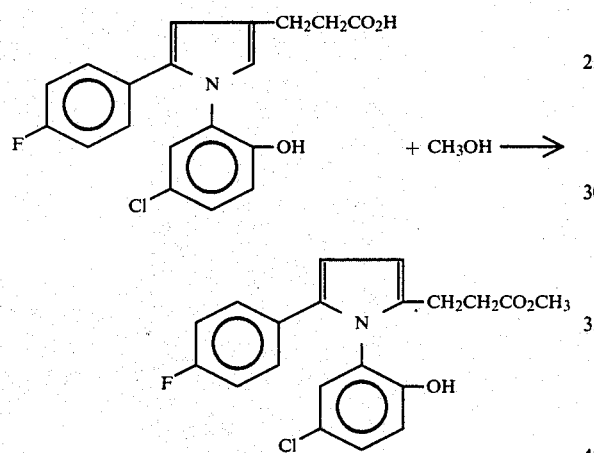

A sample of the compound of Example 1 was dissolved in methanol containing 1% concentrated sulfuric acid. The reaction mixture was heating under reflux for 7 hours. Then it was concentrated under reduced pressure. The residue was diluted with water, and the mixture was extracted with ether. The ether extract was washed with water 5% sodium bicarbonate solution and water again. Then it was dried over anhydrous sodium sulfate and concentrated to a small volume. Addition of hexane to the residue afforded the product as the methyl ester mp 182°–185°.

EXAMPLE 4

1-(5-chloro-2-hydroxyphenyl)-5-(4-fluorophenyl)-1H-pyrrole-2-propanamide

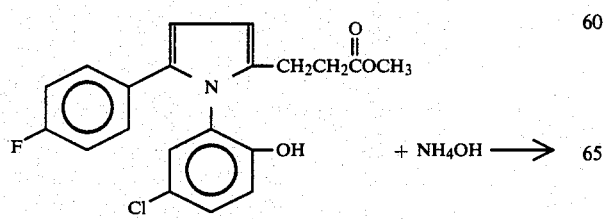

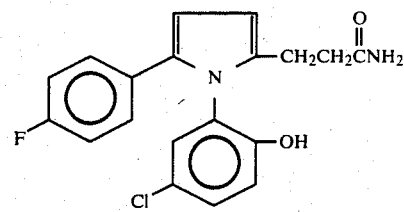

A 1.0 g sample of the methyl ester prepared in Example 3 was dissolved in 10 ml of ethanol. After 30 ml of ammoninum hydroxide was added, the reaction mixture was heated on a steam bath for 2 hours. Then it was concentrated on the steam bath in a stream of nitrogen to remove the ethanol. The residue was poured into ice water. The resultant mixture was extracted with ether. The ether extract was washed with water, dried over anhydrous sodium sulfate, and evaporated to dryness to afford a tarry product. Repeated crystallization from ether-benzene afforded the product, mp 151°–156°.

Calcd. for $C_{19}H_{16}ClFN_2O_2$ (MW 358.80): N, 7.81; Cl, 9.88. Found: N, 7.55; Cl, 9.73.

EXAMPLE 5

1-(5-chloro-2-hydroxyphenyl)-5-(4-chlorophenyl)-1H-pyrrole-2-propanoic acid

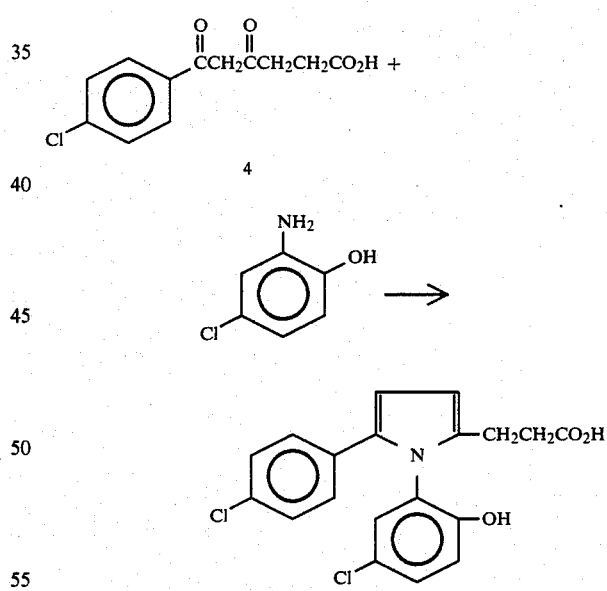

A mixture of 2.0 g of the diketoacid (4), 1.0 g of 2-amino-4-chlorophenol, 100 ml of toluene, and 40 mg of p-toluenesulfonic acid monohydrate was stirred and heated under reflux in the presence of a water separator for 17 hours. On standing at room temperature, the reaction mixture afforded the title product as a crystalline product which was collected, washed with ether and hexane, mp 175°–178°.

Calcd. for $C_{19}H_{15}NO_3Cl_2$ (MW 376.23): N, 3.72, Cl, 18.85. Found: N, 3.57; Cl, 19.07.

EXAMPLE 6

1-[2-acetyloxy)-5-chlorophenyl]-5-(4-chlorophenyl)-1H-pyrrole-2-propanoic acid

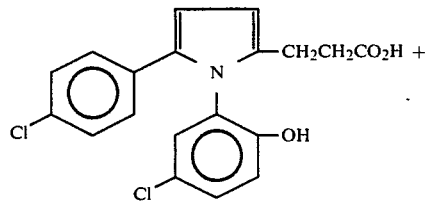

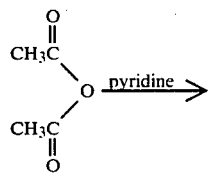

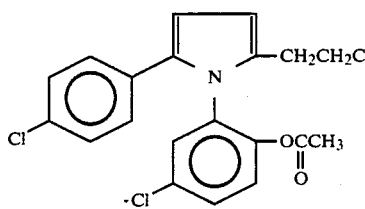

A solution of 513 mg of the compound of Example 5, 6 ml of pyridine, and 8 ml of acetic anhydride was allowed to stand at room temperature for 18 hours. The reaction mixture was poured into 120 ml of ice water. The oil that separated out was rubbed until it was transformed into a gum. The aqueous solution was decanted, and the gum was dissolved in ether. The ether solution was washed with water, dried over anhydrous sodium sulfate and evaporated to dryness to afford a viscous oil. The oil was crystallized from ether-hexane to afford the title product.

Calcd. for $C_{21}H_{17}NO_4Cl_2$ (MW 418.27): C, 60.30; H, 4.10; N, 3.35. Found: C, 60.61; H, 4.02; N, 3.36.

NMR (CDCl₃):

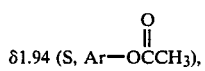

$\delta 1.94$ (S, Ar—OCCH₃), 2.65 (S, CH₂CH₂), 6.05 (d,J=4 Hz, pyrrole-H), 6.30 (d,J=4 Hz, pyrrole-H).

EXAMPLE 7

1-(5-chloro-2-hydroxyphenyl)-5-(4-methoxyphenyl)-1H-pyrrole-2-propanoic acid

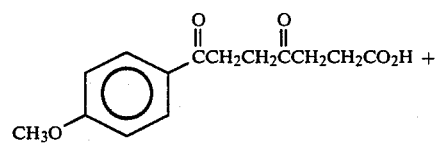

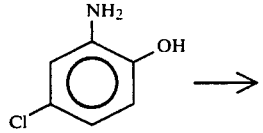

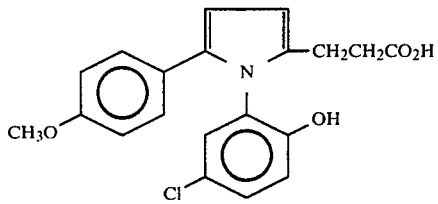

A mixture of 2.0 g of the diketoacid (5), 1.3 g of 2-amino-4-chlorophenol, 15 mg of p-toluenesulfonic acid monohydrate and 100 ml of toluene was heated under reflux in a setup containing a water separator for 18 hours. The reaction mixture was concentrated to approximately 10 ml. The cooled residue was diluted with hexane to afford a solid product. The solid was collected and crystallized from ether-hexane to afford the title product, mp 114°-118°.

Calcd. for $C_{20}H_{18}ClNO_4$ (MW 371.81): N, 3.77; Cl, 9.54. Found: N, 3.53; Cl, 9.56.

BIOLOGICAL EVALUATIONS

The compounds of the invention are evaluated with respect to 5-lipoxygenase inhibition according to the following assay procedures.

(1) Inhibition of 5-lipoxygenase, in vitro: anti-inflammatory, anti-allergy activities.

The 100,000×g supernatant fraction of Rat Basophilic Leukemia Cell Homogenate (RBL-1) serves as a 5-lipoxygenase enzyme source. The enzyme is incubated with [1-$^{14}$C]-arachidonic acid and Ca++ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to etermine the IC₅₀ value (inhibitory concentration to inhibit 50%).

(2) Inhibition of slow reacting substance (SRS) biosynthesis in cells.

SRS synthesis by Rat Basophilic Leukemia Cell (RBL-1) cells is induced by incubation of cells with ionophore A23187 alone and in combination with the test compound. The SRS released into the culture media is measured. The percent inhibition of SRS production is estimated by determining the doses of treated and control media needed in the tissue bath to produce equivalent contractions of segments of isolated guinea pig ileum. A compound that inhibits SRS biosynthesis by 50% or more is considered active at that concentration if an equivalent amount of the compound does not antagonize ileum contraction by SRS directly. If the compound directly inhibits the smooth muscle contractions, it will be considered inactive.

Initial screening doses of test compounds are $1 \times 10^{-4}M$ and $1 \times 10^{-5}M$.

The results with respect to certain of the preferred compounds of the present invention are set forth in Table I below:

TABLE I

| Compound Example No. | Rat Basophilic Leukemia Cell-Inhibition $IC_{50}(\mu M)$ | Slow Reacting Substance - % Inhibition |
|---|---|---|
| 1. | 0.83 | 82% @ 5 $\mu M$ |
| 4. | 2.40 | N.T.1 |
| 5. | 10.0 | N.T. |
| 7. | 35.0 | N.T. |

1 = not tested

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A compound of the formula:

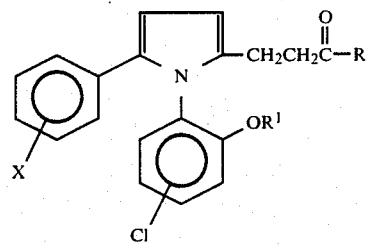

and the pharmaceutically acceptable base salts thereof wherein
R represents hydroxy, alkoxy of from 1 to 6 carbon atoms, inclusive, or amino:
$R^1$ represents hydrogen or acyl of from 2 to 7 carbon atoms, inclusive; and
X represents hydrogen, halogen, hydroxy, or alkoxy of from 1 to 6 carbon atoms, inclusive.

2. A compound according to claim 1 wherein R is hydroxy or methoxy.

3. A compound according to claim 1 wherein X is halogen.

4. A compound according to claim 3 wherein X is para-fluoro or para-chloro.

5. A compound according to claim 1 wherein $R^1$ is hydrogen.

6. A compound according to claim 1 of the formula

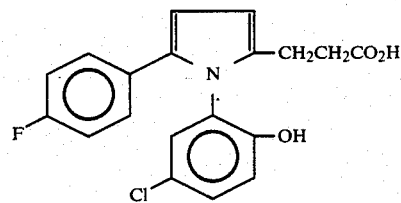

7. A pharmaceutical composition for the treatment of inflammation and allergy conditions comprising a therapeutically effective amount of a compound according to claim 1 and a pharmaceutically acceptable carrier.

8. A pharmaceutical composition according to claim 7 adapted for oral administration.

9. A method of eliciting an anti-inflmmatory or anti-allergic effect in a mammal in need thereof comprising administering thereto a therapeutically effective amount of a compound according to claim 1.

10. A method of treating asthma in a mammal in need thereof comprising administering thereto a therapeutically effective amount of a compound according to claim 1.

11. A method of treating psoriasis in a mammal in need thereof comprising administering thereto a therapeutically effective amount of a compound according to claim 1.

12. A method according to claim 11 wherein said compound is administered topically.

* * * * *

UNITED STATES PATENT AND TRADEMARK OFFICE
CERTIFICATE OF CORRECTION

PATENT NO. : 4,694,018
DATED : September 15, 1987
INVENTOR(S) : Leland J. Chinn

It is certified that error appears in the above-identified patent and that said Letters Patent are hereby corrected as shown below:

On the front page of the patent in the section that designates the assignee, reading "G. D. Serale & Co." should read -- G. D. Searle & Co. --.

Column 5, line 2, reading "alterning" should read -- altering --.

In the second formula in Column 10, under Example 5, that portion of the formula reading $\underset{CCH_2CCH_2}{\overset{O\quad O}{\|\quad\|}}$ should read $\underset{CCH_2CH_2CCH_2}{\overset{O\qquad O}{\|\qquad\|}}$ Signed and Sealed this Thirty-first Day of May, 1988

Attest:

DONALD J. QUIGG

Attesting Officer

Commissioner of Patents and Trademarks